United States Patent [19]

Chupp et al.

[11] Patent Number: 4,532,353

[45] Date of Patent: Jul. 30, 1985

[54] SUBSTITUTED BENZOTRIFLUORIDE COMPOUNDS AS CHEMICAL INTERMEDIATES AND A PROCESS FOR THEIR PREPARATION

[75] Inventors: John P. Chupp, Kirkwood; Audrey Y. Ku, Chesterfield; Thomas E. Neumann, Maryland Heights; Thomas E. Nickson, St. Charles, all of Mo.

[73] Assignee: Monsanto Co., St. Louis, Mo.

[21] Appl. No.: 504,909

[22] Filed: Jun. 16, 1983

[51] Int. Cl.$^3$ .................... C07C 87/60; C07C 85/24; C07C 85/11
[52] U.S. Cl. .................. 564/442; 564/411; 564/417
[58] Field of Search .............. 564/411, 417, 442

[56] References Cited

U.S. PATENT DOCUMENTS 2,056,899 10/1936 Hoffa et al. .................. 564/442

FOREIGN PATENT DOCUMENTS 0038465 10/1981 European Pat. Off. ........... 564/417

OTHER PUBLICATIONS

Chem. Abs. 54, 4430(e), (1960).
Morrison et al., "Organic Chemistry" (3rd ed.) Allyn and Bacon, Boston, 1973, Chapter 11, p. 346; Chapter 22, p. 737.

Primary Examiner—Charles F. Warren
Assistant Examiner—Harry B. Shubin
Attorney, Agent, or Firm—Robert B. Martin

[57] ABSTRACT

This invention pertains to two substituted benzotrifluoride compounds useful as chemical intermediates for a new class of 2-haloacetanilide herbicides and a process for making these intermediates. The process generally involves nitration and reduction of the corresponding benzotrifluoride compound.

8 Claims, No Drawings

SUBSTITUTED BENZOTRIFLUORIDE COMPOUNDS AS CHEMICAL INTERMEDIATES AND A PROCESS FOR THEIR PREPARATION

FIELD OF THE INVENTION

The invention herein pertains to substituted benzotrifluoride compounds useful as chemical intermediates and a process for their preparation. The chemical intermediates are useful for the preparation of substituted anilines which are precursors for a new class of 2-haloacetanilide herbicides.

BACKGROUND OF THE INVENTION

It has recently been discovered that a certain class of 2-haloacetanilide herbicides are particularly useful in safely controlling hard-to-kill perennial weeds such as quackgrass, nutsedges and many others in the presence of a variety of crops including cotton, corn, and soybean. This new class of herbicides is described and claimed in Brazilian Pat. No. 887,997 issued Sept. 18, 1981. Two particularly effective herbicides within this class are N-(ethoxymethyl)-2'-trifluoromethyl-6'-methyl-2-chloroacetanilide and N-(ethoxymethyl)-2'-trifluoro-methyl-6'-ethyl-2-chloroacetanilide.

The present invention relates to two intermediates in the production of compounds within this new class of herbicides. The present invention also relates to a process for preparing these two intermediates. The process generally comprises nitration of the a substituted benzotrifluoride compound. Electrophilic substitution such as nitration, sulfonation, etc. of various types of substituted benzene compounds is known in the art. It is also known that substituents on the benzene ring can affect both the reactivity and orientation of electrophilic substitution. Certain substituents can increase the reactivity of the benzene ring by donating electron density to the ring inductively or by resonance. Other groups withdraw electron density from the ring and thus reduce the reactivity of the ring.

Ring substituents can either direct electrophilic substitution at the ortho, para, or meta positions. With a plurality of substituents, the substituents can either reinforce or oppose each others directive influence. However, in directing electrophilic substitution, activating substituents generally prevail over deactivating substituents.

It is an object of the present invention to provide new compounds useful in the production of compounds within a new class of 2-haloacetanilide herbicides.

It is another object of this invention to provide a process for producing these new intermediate compounds.

It is another object of this invention to provide a new aromatic nitration directing system.

Other objects and advantages will become apparent from the following disclosure.

SUMMARY OF THE INVENTION

The present invention relates to two novel substituted benzotrifluoride compounds and a process for making these compounds. The substituted benzotrifluoride compounds are chemical intermediates in the production of substituted anilines which are precursors for the preparation of compounds within a new class of 2-haloacetanilide herbicides.

The novel substituted benzotrifluoride compounds of this invention are 3-methyl-5-amino benzotrifluoride and 3-ethyl-5-amino benzotrifluoride.

The process of the present invention for making the novel substituted benzotrifluoride compounds generally involves nitration of the corresponding halogen substituted benzotrifluoride compound and hydrogenation of the nitrated product to simultaneously hydrodehalogenate the ring and reduce the nitro group to form the intermediate compound.

Starting compounds which can be used for making the intermediates of the present invention are 3-methyl benzotrifluoride and 3-ethyl benzotrifluoride. The 3-methyl benzotrifluoride can be prepared by known literature methods. The 3-ethyl benzotrifluoride can be prepared generally by reduction of commercially available trifluoromethyl acetophenone. To form the intermediate compounds, the starting compounds, 3-methyl benzotrifluoride or 3-ethyl benzotrifluoride are halogenated, conveniently chlorinated, conveniently with a catalyst, to form a mixture consisting substantially of the 2, 4, or 6 mono chloro isomers. The mixture is then nitrated, conveniently with nitric acid. Most of the nitration is surprisingly directed to the 5-position. The reaction products are then hydrogenated to form the corresponding intermediate compounds.

To form compounds within the new class of 2-haloacetanilide herbicides, the intermediate compounds are sequentially acetylated, nitrated, deacetylated, diazotized, and reduced to form the precursor aniline, 2-amino-3-alkyl benzotrifluoride. The precursor aniline can be converted into compounds within the new class of 2-haloacetanilide herbicides according to known procedures. A more thorough disclosure of the present invention is presented in the detailed description which follows.

DETAILED DESCRIPTION

The present invention relates to two novel substituted benzotrifluoride compounds and a process for making these compounds. The substituted benzotrifluoride compounds are useful as chemical intermediates in the production of precursor anilines used in the preparation of compounds within a new class of 2-haloacetanilide herbicides.

The novel substituted benzotrifluoride compounds of this invention are (a) 3-methyl-5-amino benzotrifluoride (1-trifluoromethyl-3-methyl-5-amino-benzene) hereinafter referred to as MAB and (b) 3-ethyl-5-amino benzotrifluoride (1-trifluoromethyl-3-ethyl-5-amino benzene) hereinafter referred to as EAB. The compounds have the following formula:

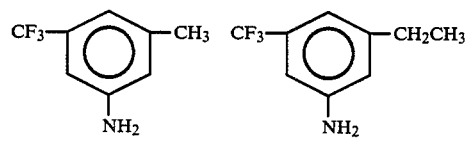

(a)       (b)

The process of the present invention for making the novel substituted benzotrifluoride compounds generally involves the steps of nitrating the corresponding halogen substituted benzotrifluoride compound and hydrogenating the nitrated product to simultaneously hydrodehalogenate the ring and reduce the nitro group to form the intermediate compounds MAB or EAB.

Starting compounds which can be used in the preparation of the intermediate compounds are 3-methyl benzotrifluoride and 3-ethyl benzotrifluoride. The 3-methyl benzotrifluoride can be prepared by reacting a Grignard reagent of m-trifluoromethyl phenyl-magnesium bromide with dimethyl sulfate by the procedures set forth in J.A.C.S. 65 389 (1943). The 3-methyl benzotrifluoride can also be prepared by reacting m-iodotoluene with the sodium salt of trifluoromethyl acetic acid and copper iodide. (Chem Letters 1719, 1981). The 3-ethyl benzotrifluoride can be prepared by reduction of commercially available m-trifluoromethyl acetophenone following known laboratory procedures. Other ways of making these compounds will be known to those skilled in the art.

The starting compounds, 3-methyl benzotrifluoride or 3-ethyl benzotrifluoride, are then halogenated, conveniently chlorinated, conveniently with a catalyst, to form a mixture consisting substantially of the 2, 4, and 6 mono chloro isomers. It will be obvious to one skilled in the art that bromine or iodine may also be used as the halogenating agent. The chlorination can be accomplished by reacting the starting compound with chlorine gas in the presence of a suitable catalyst at an elevated temperature. The chlorination can be accomplished without a solvent. However, if desired, the starting compound may be dissolved in a suitable inert solvent, such as methylene chloride. The reaction is conveniently carried out at a temperature from about 40° C. to about 50° C. A suitable chlorination catalyst is anhydrous ferric chloride but other chlorination catalysts may also be utilized. The starting compound is conveniently reacted with about a 10% molar excess of chlorine gas. The chlorination reaction generally results in the formation of about an 85% yield of mono chlorinated product comprising generally about 45% of the 2- and 6-chloro isomers and about 40% of the 4-chloro isomer. Because of the deactivating nature of the chlorine atom and the trifluoromethyl radical, only about 10% of the dichloro isomer is formed in the chlorination reaction.

The mixture of the 2, 4, and 6 mono chloro isomers of the substituted benzotrifluoride may then be conveniently nitrated with a suitable nitrating agent such as nitric acid, oxides of nitrogen, e.g. dinitrogen pentoxide or nitronium tetrafluoroborate. The crude mixture can be nitrated or the mixture purified and the purified mixture nitrated. The mixture may be conveniently nitrated with nitric acid. Conveniently, nitration is accomplished with a molar excess of concentrated nitric acid, e.g. concentration of 80% or greater. The nitration may be conveniently accomplished by slowly adding the mixture of the substituted benzotrifluoride to about 1.1 to about 10 molar equivalents of nitric acid, e.g. about 1.1 to about 10 moles of nitric acid per mole of substituted benzotrifluoride. The nitric acid is conveniently concentrated nitric acid, e.g. 98%, at a temperature of about −5° C. to about 25° C. If it is desired to use less than about 3 molar equivalents of concentrated nitric acid, it is desirable that a suitable acid cosolvent be used during nitration, such as oleum, sulfuric acid, hydrofluoric acid or phosphoric acid. Concentrated sulfuric acid can be conveniently used as a cosolvent to sequester the water formed during the reaction thereby maintaining a concentrated solution of the nitric acid to facilitate the rate of nitration. The mixture may be nitrated with or without a suitable inert organic solvent, such as 1,2 dichloroethane, nitromethane, carbon tetrachloride, sulfolane or methylene chloride.

Conveniently, a 10-fold molar excess of 98% nitric acid is placed in an appropriate nitration vessel. The substituted benzotrifluoride is then slowly added dropwise to the acid while maintaining the temperature, preferably at about −5° C. to about 10° C. After completion of the addition, the solution is stirred until completion of the mononitration reaction.

Surprisingly, about 70% to about 77% of the nitration is in the 5-position. After the reaction is completed, the nitration product is conveniently separated from the acid by suitable laboratory methods, such as solvent solution extraction with a suitable inert organic solvent, such as methylene chloride, optimally following water dilution of the reaction mixture.

The nitration product is then hydrogenated to hydrodehalogenate the aromatic ring and reduce the nitro group to form the corresponding intermediate compound MAB or EAB. The hydrogenation can be conveniently accomplished by dissolving the nitration product in a suitable inert solvent. Among the wide variety of suitable solvents for this process are various polar solvents including alcohols, ethers, hydrocarbons, water, and the like. Convenient are alcohols, such as methanol or ethanol optionally aqueous. In general, the concentration of the nitrated reactants in the solvent can range from about 20% to about 50% by weight.

The reaction mixture preferably also includes an appropriate hydrogen halide scavenger, which can be selected from a wide variety of organic and inorganic bases. The scavenger neutralizes hydrogen halide as it is formed and solvent-soluble scavengers are preferred. Typical scavengers include ammonia (e.g., as 29% aqueous solution) trimethylamine, triethylamine, pyridine and di-isopropylethylamine. Trimethylamine and triethylamine are desirable scavengers. The scavenger conveniently is present in the reaction mixture at a level of about 1.2 moles per mole of nitrated mixture.

The reaction mixture also conveniently includes a hydrogenation catalyst. Suitable hydrogenation catalysts are metal catalysts, such as palladium, platinum, rhodium, nickel, and the like, which most often are available on porous supports. Palladium on carbon catalysts are commercially available in concentrations of 1% to 10% palladium. The supported catalysts are generally present in amounts less than 10% by weight of the reaction mixture.

The above-described reagents are conveniently combined in a suitable vessel equipped with means for stirring and introducing gaseous hydrogen. The hydrogenation is conveniently carried out at a temperature of about 25° C. to about 100° C. and under a hydrogen pressure from atmospheric to about 68 atmospheres. The hydrogenation product is conveniently separated by solvent extraction with a suitable organic solvent, such as methylene chloride. The hydrogenation of the nitrated product hydrodehalogenates the aromatic ring and reduces the nitro group to an amino group.

The intermediate MAB or EAB may then be separated from the other reaction products by a suitable separation technique, such as fractional distillation. For example, a column having 40 theoretical plates and a reflux ratio of 6:1 can give about a 70% yield of MAB at about 98% assay.

An alternative method for making 3-methyl-5-amino benzotrifluoride involves generally chloromethylation of o-chlorobenzotrifluoride and nitration and reduction of the chloromethylated product. Chloromethylation of o-chlorobenzotrifluoride can be accomplished following the procedure set forth in German Pat. No. 1,568,938 or U.S. Pat. No. 3,465,051. The chloromethylation reaction results in the formation of a mixture of about 89% 6-chloro-3-chloromethyl benzotrifluoride and about 11% 2-chloro-3-chloromethyl benzotrifluoride. This mixture is then nitrated, conveniently with nitric acid or an acid mixture comprising nitric acid and oleum or sulfuric acid. Conveniently, the benzotrifluoride mixture is slowly added to an acid mixture comprising a molar excess of concentrated nitric acid, e.g. about 1.25 to about 5 molar equivalents of 98% nitric acid, and a molar excess of oleum, e.g. about 1.25 molar equivalents of oleum (30–65% $SO_3$). The nitration is conveniently carried out at a temperature from about 0° C. to about 50° C., suitably about 35° C. After completion of the addition, the reaction mixture is stirred for a short period of time, e.g. about 3 hours, until completion of the nitration reaction which can be followed by glc. The nitration product may be separated by standard laboratory methods, e.g. solvent extraction using a suitable organic solvent, such as dichloromethane or ethyl acetate. Surprisingly, this alternative method results in substantially all of the nitration occurring in the 5-position. Yield of the 5-nitro isomer is normally about 95% at high assay, e.g. about 96% assay. The nitration product is then hydrogenated following the above-described procedure to hydrodehalogenate the aromatic ring and reduce the nitro group and the chloromethyl group to form the corresponding intermediate compound, MAB.

The intermediate compounds of the present invention can be converted into compounds within the new class of 2-haloacetanilide herbicides by first forming the corresponding precursor aniline. To form the precursor aniline, the amino group is acetylated by known procedures to form the corresponding acetanilide. The intermediate is first conveniently dissolved in a suitable, organic solvent, such as ethylene dichloride, o-chlorobenzene, or dichloromethane. The mixture is heated from about 40° C. to about 80° C. and a slight molar excess from about 0.05% to about 20% of acetic anhydride or acetyl chloride is added with stirring. The mixture is then stirred for a couple of hours to form the corresponding acetanilide.

The corresponding acetanilide is then nitrated. The acetylation should be complete before beginning the nitration. This can be checked by glc analysis. If desired, the acetanilide may be isolated prior to nitration. The acetanilide may be nitrated with or without an organic solvent. The acetanilide is conveniently nitrated by first slowly adding a molar excess of about 7.0 of concentrated sulfuric acid to the acetanilide solution. The sulfuric acid functions both as a solvent and a dehydrating agent to remove water formed during the reaction. The reaction medium is cooled to maintain the temperature preferably below 35° C. After addition of the sulfuric acid, a mixture of concentrated nitric acid and concentrated sulfuric acid is slowly added to the mixture while the temperature is maintained preferably below 35° C. The mixture conveniently comprises a molar excess of about 1.1 of nitric acid and a ratio of nitric acid to sulfuric acid of about 1:4. The mixture is stirred for about 1.5 to about 2.5 hours. Longer stirring times may reduce yield. The mixture is then poured over ice and extracted with a suitable organic solvent, such as ethyl acetate. Substantially all of the nitration of the acetanilide occurs in the 4-position.

The nitrated acetanilide compounds can then be readily converted into the corresponding precursor anilines. The acetamido group can be removed following standard laboratory procedures. The acetanilide is conveniently dissolved in a suitable alcohol, such as ethanol, and reacted with concentrated sulfuric acid, water and sodium nitrite to form the corresponding nitro benzene compound, 1-(trifluoromethyl)-2-nitro-3-alkyl benzene. The nitro benzene compound can then be reduced to the precursor aniline by hydrogenation with a palladium on carbon catalyst.

The precursor aniline may then be converted to compounds within the new class of tertiary 2-halo-acetanilide herbicides by a variety of methods. For example, the 2-haloacetanilide may be prepared by haloacetylation of the precursor aniline by known procedures to form secondary 2-haloacetanilide which is then N-alkylated to form compounds within the new class of tertiary 2-haloacetanilide herbicides. The haloacetylation of the aniline can be accomplished by adding a slight molar excess of chloroacetyl chloride to the aniline in a suitable organic solvent, such as toluene, and heating the solution to reflux for a short period of time. The secondary 2-haloacetanilide is then N-alkylated according to known procedures.

A suitable N-alkylation process is described in detail in U.S. Pat. No. 4,258,196. A modified N-alkylation process is described in U.S. Pat. No. 4,284,564. The tertiary 2-haloacetanilides may also be made by a transetherification process. This process is described in U.S. Pat. No. 4,296,254. The precursor aniline may also be converted into tertiary 2-haloacetanilides by the procedure disclosed in Brazilian Pat. No. 887,997. These patents are incorporated herein by reference.

The following examples are presented to illustrate the present invention as well as some of the various embodiments of the invention. These examples are presented as being illustrative of the novel process of the invention and are not intended to be a limitation as to the scope thereof.

EXAMPLE I

Mixture of 2, 4 and 6 Chloro-3-Methyl Benzotrifluoride 64 gms (0.4 mole) of 3-methyl benzotrifluoride was placed in 500 ml flask with 0.16 gms of $FeCl_3$ and 0.17 gms of Fe and heated to about 45° C. 32 gms (0.45 moles) of chlorine gas was then bubbled through solution. Yield 73 gms of a yellow-amber colored oil, which glc and $^{19}F$ NMR data indicated was a mixture comprised of about 85% of monochloro-3-methyl benzotrifluoride; 10% dichloro-3-methyl benzotrifluoride; and 4% 3-methyl benzotrifluoride.

EXAMPLE II

Mixture of 2, 4 and 6 Chloro-3-Methyl-5-Nitro Benzotrifluoride 72 gms of the crude mixture of 2, 4, and 6 mono chloro 3-methyl benzotrifluoride (0.37 moles) from Example I was added dropwise to 200 gms of 98% $HNO_3$ at about $-5°$ C. to 0° C. over a period of about 1 hour. After addition, solution was stirred for an additional 20 minutes. The solution was then washed with ice water and solvent extracted with $CH_2Cl_2$ to give 87 gms of an amber colored liquid. The liquid was distilled at 100°–110° C./(<0.1 mm) to give 84.5 gms of a yellow colored liquid (96% yield)

EXAMPLE III

3-Methyl-5-Amino Benzotrifluoride 84.5 gms of the nitrated product from Example II (0.35 moles) was added to 220 ml of MeOH in a pressure vessel with 40 gms of triethyl amine and a pinch of palladium on carbon catalyst. The vessel was then pressured to 54.4 atms with hydrogen gas and maintained at a temperature of 25° C. to 96° C. over a period of about 5 hours. The MeOH was then stripped under vacuum and product was washed with CH$_2$Cl$_2$ and stripped to give 59 gms of an amber colored liquid (94.8% yield). 58 gms of the liquid was distilled in a 10 tray oldershaw column at reflux ratio of 7:1 to give 34.9 gms (60% yield) of an amber colored liquid, 3-methyl-5-amino benzotrifluoride; bp 81° C. at 5.1 mm (gc assay >95%).

EXAMPLE IV

A Mixture of 2- and 4-Chloro-3-Triflouromethyl Benzyl Chloride

A 500 ml flask was charged with 200 gms (2.5 moles) of chloromethyl methyl ether and 225 gms (1.25 moles) o-chlorobenzotrifluoride. This solution was brought to 35° C. and 175 gms (1.5 moles) of chlorosulfonic acid was added over a 20 minute period. The reaction temperature was slowly brought to 75° C. (over 3 hours) and held there for 6 hours. The dark solution was cooled to 30° C., quenched over 500 gms of ice, shaken, and separated. The bottom layer was drawn off and the top aqueous layer was washed once with 75 ml of methylene chloride. Both organic layers were combined and stirred vigorously with 250 ml of 25% NaOH for 3 hours. The final mixture was separated by dilution with 500 ml of water and the bottom organic layer was dried (Na$_2$SO$_4$), filtered and distilled to give:

I. 50.6 gms of o-chlorobenzotrifluoride; b.p. 60°–62° C./35 mm

II. 135.1 gms of a mixture of 2- and 4-chloro-3-trifluoromethyl benzyl chloride; b.p. 42° C./0.2 mm (61% yield).

EXAMPLE V

A Mixture of 2 and 4 Chloro-3-Trifluoromethyl-5-Nitro Benzylchloride 40 gms of 62% oleum is added slowly to 60 gms of 98% HNO$_3$ so that the temperature never goes above 40° C. Then 46 gms (0.2 moles) of the mixture from Example IV is added slowly to the acid mixture over a 40 minute period at a temperature of 0° C. The reaction mixture was allowed to stir for 5 hours while coming to room temperature. The final 2 layer system was separated and the bottom aqueous layer was poured over ice/water. The aqueous phase was washed with 50 ml CH$_2$Cl$_2$. The organic layers were then combined and washed once with water and once with 10% NaOH. The organic layer was then dried with Na$_2$SO$_4$, filtered and concentrated to 53.5 gms (97.6% yield) of a bright yellow viscous oil (gc assay 96%).

EXAMPLE VI

3-Methyl-5-Amino Benzotrifluoride

At room temperature, 32.3 gms of crude nitrated product from Example V was added to a mixture of 150 ml MeOH and 30 gms (2.5 eq) of trimethylamine. The dark solution was charged with 1.6 gms of 50% wet 5% Pd/C catalyst and hydrogenated for 48 hours at 60° C. with hydrogen at 4 atms. The final solution was concentrated by distilling about half of the MeOH, diluted with 250 ml H$_2$O and washed 3 times with 100 ml CH$_2$Cl$_2$. All of the organic extractions were combined, dried (Na$_2$SO$_4$), filtered and concentrated to 24 gms of a dark liquid which was Kugelrohr distilled at 95°–110° C./32 mm to 17.6 gms of light yellow colored crystals of 3-methyl-5-amino benzotrifluoride; mp 27°–28° C. (83% yield).

Although this invention has been described with respect to specific embodiments, the details hereof are not to be construed as limitations, for it will be apparent that various equivalents, changes and modifications may be resorted to without departing from the spirit and scope thereof and it is understood that such equivalent embodiments are intended to be included within the scope of this invention.

We claim:

1. A process for preparing the compound having the formula:

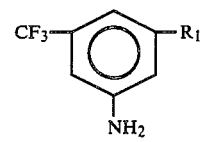

I which comprises the steps of
(a) nitrating the compound having the formula:

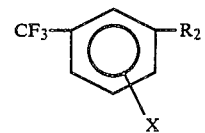

II and
(b) hydrogenating the nitrated product of step (a) wherein the above formula R$_1$ is methyl ethyl, R$_2$ is chloro-methyl and X is chloromethyl and X is chloro, bromo, or iodo.

2. The process of claim 1 wherein the compound of formula II is nitrated with about 1.1 to about 10 molar equivalents of concentrated nitric acid.

3. The process of claim 1 wherein the compound of formula II is nitrated with a mixture of concentrated nitric acid and oleum.

4. The process of claim 1 wherein the compound of formula II is nitrated with a mixture of concentrated nitric acid and concentrated sulfuric acid.

5. The process of claim 1 wherein the nitrated product of step (a) is hydrogenated with hydrogen gas in a polar solvent with a hydrogenation catalyst and a halide scavenger.

6. The process of claim 5 wherein said polar solvent comprises alcohol.

7. The process of claim 5 wherein said hydrogenation catalyst is selected from the group consisting of palladium, platinum, rhodium and nickel.

8. The process of claim 5 wherein said halide scavenger is selected from the group consisting of ammonia, trimethylamine, triethylamine, pyridine and di-isopropyl-ethylamine.

* * * * *

UNITED STATES PATENT AND TRADEMARK OFFICE
CERTIFICATE OF CORRECTION

PATENT NO. : 4,532,353
DATED : July 30, 1985
INVENTOR(S) : John P. Chupp, Audrey Y. Ku, Thomas E. Neumann and Thomas E. Nickson It is certified that error appears in the above-identified patent and that said Letters Patent is hereby corrected as shown below:

Claim 1 (column 8, lines 42 turough 45 should read as follows:

"(b) hydrogenating the nitrated product of step (a) wherein the above formula $R_1$ is methyl, $R_2$ is chloromethyl and X is chloro, bromo, or iodo."

Signed and Sealed this

Seventeenth Day of December 1985

[SEAL]

Attest:

DONALD J. QUIGG

Attesting Officer

Commissioner of Patents and Trademarks